US010682435B2

(12) United States Patent
Mark et al.

(10) Patent No.: US 10,682,435 B2
(45) Date of Patent: Jun. 16, 2020

(54) METHOD FOR PRODUCING WATER-ABSORBING POLYMER PARTICLES BY SUSPENSION POLYMERIZATION

(71) Applicant: BASF SE, Ludwigshafen (DE)

(72) Inventors: Tina Mark, Hassloch (DE); Thomas Daniel, Waldsee (DE); Stefan Molter, Maxdorf (DE); Erich Lutz, Altrip (DE)

(73) Assignee: BASF SE, Ludwigshafen (DE)

( * ) Notice: Subject to any disclaimer, the term of this patent is extended or adjusted under 35 U.S.C. 154(b) by 123 days.

(21) Appl. No.: 15/552,844

(22) PCT Filed: Feb. 17, 2016

(86) PCT No.: PCT/EP2016/053297
§ 371 (c)(1),
(2) Date: Aug. 23, 2017

(87) PCT Pub. No.: WO2016/135011
PCT Pub. Date: Sep. 1, 2016

(65) Prior Publication Data
US 2018/0043051 A1 Feb. 15, 2018

(30) Foreign Application Priority Data

Feb. 27, 2015 (EP) ..................................... 15156847

(51) Int. Cl.
C08F 2/14 (2006.01)
A61L 15/60 (2006.01)
C08F 2/18 (2006.01)
C08F 220/06 (2006.01)
C08F 222/38 (2006.01)

(52) U.S. Cl.
CPC ................ *A61L 15/60* (2013.01); *C08F 2/14* (2013.01); *C08F 2/18* (2013.01); *C08F 220/06* (2013.01); *C08F 222/385* (2013.01)

(58) Field of Classification Search
CPC .. C08F 2/14; C08F 2/18; C08F 120/06; C08F 6/18; C08F 220/06; C08F 222/385; C08J 3/245; A61L 15/60

USPC .......................................................... 524/457
See application file for complete search history.

(56) References Cited

U.S. PATENT DOCUMENTS

| 8,399,585 B2* | 3/2013 | Lopez Villanueva .. A61L 15/22 502/402 |
| 9,138,722 B2* | 9/2015 | Tanimura ................... C08F 2/32 |
| 2010/0019198 A1* | 1/2010 | Stueven ................... A61L 15/60 252/194 |
| 2010/0069235 A1 | 3/2010 | Funk |
| 2011/0071267 A1 | 3/2011 | Lopez Villanueva et al. |
| 2016/0280825 A1 | 9/2016 | Bauer et al. |
| 2017/0266640 A1* | 9/2017 | Mark ......................... C08F 2/18 |
| 2018/0030218 A1* | 2/2018 | Mark ...................... C08F 220/06 |

FOREIGN PATENT DOCUMENTS

| EP | 1 837 348 A1 | 9/2007 |
| JP | S63218702 A | 9/1988 |
| JP | 2010502415 A | 1/2010 |
| WO | WO-2006/014031 A1 | 2/2006 |
| WO | WO-2008/068208 A1 | 6/2008 |
| WO | WO-2011/023572 A1 | 3/2011 |
| WO | WO-2011/065368 A1 | 6/2011 |
| WO | WO-2015/062883 A2 | 5/2015 |

OTHER PUBLICATIONS

Buchholz, Fredric L., et al., "Commercial Processes for the Manufacture of Superabsorbent Polymers," Modern Superabsorbent Polymer Technology, New York: John Wiley & Sons, Inc., 1998, pp. 69-117.
International Search Report for Patent Application No. PCT/EP2016/053297, dated Jun. 8, 2016.

* cited by examiner

*Primary Examiner* — Hannah J Pak
(74) *Attorney, Agent, or Firm* — Marshall, Gerstein & Borun LLP

(57) ABSTRACT

A process for producing water-absorbing polymer particles by suspension polymerization, wherein the polymerization is conducted in the presence of dissolved oxygen.

12 Claims, No Drawings

METHOD FOR PRODUCING WATER-ABSORBING POLYMER PARTICLES BY SUSPENSION POLYMERIZATION

CROSS-REFERENCE TO RELATED APPLICATIONS

This application is the U.S. National Stage application of International Patent Application No. PCT/EP2016/053293, filed Feb. 17, 2016, which claims the benefit of European Patent Application No. 15156847.4, filed Feb. 27, 2015.

The present invention relates to a process for producing water-absorbing polymer particles by suspension polymerization, wherein the polymerization is conducted in the presence of dissolved oxygen.

The production of water-absorbing polymer particles is described in the monograph "Modern Superabsorbent Polymer Technology", F. L. Buchholz and A. T. Graham, Wiley-VCH, 1998, pages 69 to 117. The water-absorbing polymer particles are typically produced by solution polymerization or suspension polymerization.

Being products which absorb aqueous solutions, water-absorbing polymers are used to produce diapers, tampons, sanitary napkins and other hygiene articles, but also as water-retaining agents in market gardening.

The properties of the water-absorbing polymers can be adjusted via the level of crosslinking. With increasing level of crosslinking, there is a rise in gel strength and a fall in absorption capacity.

To improve the use properties, for example permeability in the swollen gel bed in the diaper and absorption under pressure, water-absorbing polymer particles are generally surface postcrosslinked. This increases only the level of crosslinking of the particle surface, and in this way it is possible to at least partly decouple absorption under pressure and centrifuge retention capacity.

JP S63-218702 describes a continuous process for producing water-absorbing polymer particles by suspension polymerization.

WO 2006/014031 A1 describes a process for producing water-absorbing polymer particles by suspension polymerization. At the high temperatures in the thermal postcrosslinking, the fraction of hydrophobic solvent is driven out.

WO 2008/068208 A1 likewise relates to a process for producing water-absorbing polymer particles having a low proportion of hydrophobic solvents by suspension polymerization.

It was an object of the present invention to provide an improved process for producing water-absorbing polymer particles by suspension polymerization, wherein the water-absorbing polymer particles are to have a high absorption capacity, a narrow particle size distribution and a rapid absorption.

The object was achieved by a process for producing water-absorbing polymer particles by polymerizing a monomer solution comprising
a) at least one ethylenically unsaturated monomer which bears acid groups and may have been at least partly neutralized,
b) optionally one or more crosslinkers,
c) at least one initiator,
d) optionally one or more ethylenically unsaturated monomers copolymerizable with the monomers mentioned under a) and
e) optionally one or more water-soluble polymers,
with the monomer solution suspended in a hydrophobic organic solvent during the polymerization, and being agglomerated in the hydrophobic organic solvent during or after the polymerization, wherein the polymerization is conducted in the presence of dissolved oxygen.

The total oxygen concentration $c_{tot1}$ immediately prior to the polymerization is preferably at least 2 ppm, more preferably from 4 to 12 ppm, most preferably from 5 to 10 ppm.

The oxygen concentration in the hydrophobic organic solvent $c_{org1}$ immediately prior to the polymerization is preferably at least 2 ppm, more preferably from 4 to 12 ppm, most preferably from 5 to 10 ppm.

The oxygen concentration of the monomer solution $c_{M1}$ immediately prior to the polymerization is preferably up to 10 ppm, more preferably from 2 to 9 ppm, most preferably from 3 to 8 ppm.

In a preferred embodiment of the present invention, the polymer particles obtained after the polymerization are agglomerated in the hydrophobic organic solvent with addition of a second monomer solution.

The total oxygen concentration $c_{tot2}$ immediately prior to the agglomeration is preferably less than 4 ppm, more preferably less than 3 ppm, most preferably less than 2 ppm.

The oxygen concentration in the hydrophobic organic solvent $c_{org2}$ immediately prior to the agglomeration is preferably less than 2 ppm, more preferably less than 1 ppm, most preferably less than 0.5 ppm.

The oxygen concentration of the monomer solution $c_{M2}$ immediately prior to the agglomeration is preferably less than 12 ppm, more preferably less than 9 ppm, most preferably less than 6 ppm.

The present invention is based on the finding that the dissolved oxygen content prior to the polymerization has a considerable influence on the formation of agglomerates of an undesirably large size. In addition, the absorption capacity can be increased by lowering the oxygen content in the agglomeration.

The production of the water-absorbing polymer particles is elucidated hereinafter:

The monomers a) are preferably water-soluble, i.e. their solubility in water at 23° C. is typically at least 1 g/100 g of water, preferably at least 5 g/100 g of water, more preferably at least 25 g/100 g of water and most preferably at least 35 g/100 g of water.

Suitable monomers a) are, for example, ethylenically unsaturated carboxylic acids, such as acrylic acid, methacrylic acid and itaconic acid. Particularly preferred monomers are acrylic acid and methacrylic acid. Very particular preference is given to acrylic acid.

Further suitable monomers a) are, for example, ethylenically unsaturated sulfonic acids, such as styrenesulfonic acid and 2-acrylamido-2-methylpropanesulfonic acid (AMPS).

Impurities can have a considerable influence on the polymerization. The raw materials used should therefore have a maximum purity. It is therefore often advantageous to specially purify the monomers a). Suitable purification processes are described, for example, in WO 2002/055469 A1, WO 2003/078378 A1 and WO 2004/035514 A1. A suitable monomer a) is, for example, an acrylic acid purified according to WO 2004/035514 A1 and comprising 99.8460% by weight of acrylic acid, 0.0950% by weight of acetic acid, 0.0332% by weight of water, 0.0203% by weight of propionic acid, 0.0001% by weight of furfurals, 0.0001% by weight of maleic anhydride, 0.0003% by weight of diacrylic acid and 0.0050% by weight of hydroquinone monomethyl ether.

The proportion of acrylic acid and/or salts thereof in the total amount of monomers a) is preferably at least 50 mol %, more preferably at least 90 mol %, most preferably at least 95 mol %.

The acid groups of the monomers a) may have been partly neutralized. The neutralization is conducted at the monomer stage. This is typically accomplished by mixing in the neutralizing agent as an aqueous solution or else preferably as a solid. The degree of neutralization is preferably from 25 to 95 mol %, more preferably from 30 to 80 mol % and most preferably from 40 to 75 mol %, for which the customary neutralizing agents can be used, preferably alkali metal hydroxides, alkali metal oxides, alkali metal carbonates or alkali metal hydrogencarbonates and also mixtures thereof. Instead of alkali metal salts, it is also possible to use ammonium salts. Particularly preferred alkali metals are sodium and potassium, but very particular preference is given to sodium hydroxide, sodium carbonate or sodium hydrogencarbonate and also mixtures thereof.

The monomers a) typically comprise polymerization inhibitors, preferably hydroquinone monoethers, as storage stabilizers.

The monomer solution comprises preferably up to 250 ppm by weight, preferably at most 130 ppm by weight, more preferably at most 70 ppm by weight, and preferably at least 10 ppm by weight, more preferably at least 30 ppm by weight and especially around 50 ppm by weight, of hydroquinone monoether, based in each case on the unneutralized monomer a). For example, the monomer solution can be prepared by using an ethylenically unsaturated monomer bearing acid groups with an appropriate content of hydroquinone monoether.

Preferred hydroquinone monoethers are hydroquinone monomethyl ether (MEHQ) and/or alpha-tocopherol (vitamin E).

Suitable crosslinkers b) are compounds having at least two groups suitable for crosslinking. Such groups are, for example, ethylenically unsaturated groups which can be polymerized free-radically into the polymer chain, and functional groups which can form covalent bonds with the acid groups of the monomer a). In addition, polyvalent metal salts which can form coordinate bonds with at least two acid groups of the monomer a) are also suitable as crosslinkers b).

Crosslinkers b) are preferably compounds having at least two polymerizable groups which can be polymerized free-radically into the polymer network. Suitable crosslinkers b) are, for example, methylenebisacrylamide, ethylene glycol dimethacrylate, diethylene glycol diacrylate, polyethylene glycol diacrylate, allyl methacrylate, trimethylolpropane triacrylate, triallylamine, tetraallylammonium chloride, tetraallyloxyethane, as described in EP 0 530 438 A1, di- and triacrylates, as described in EP 0 547 847 A1, EP 0 559 476 A1, EP 0 632 068 A1, WO 93/21237 A1, WO 2003/104299 A1, WO 2003/104300 A1, WO 2003/104301 A1 and DE 103 31 450 A1, mixed acrylates which, as well as acrylate groups, comprise further ethylenically unsaturated groups, as described in DE 103 31 456 A1 and DE 103 55 401 A1, or crosslinker mixtures, as described, for example, in DE 195 43 368 A1, DE 196 46 484 A1, WO 90/15830 A1 and WO 2002/032962 A2.

Preferred crosslinkers b) are pentaerythrityl triallyl ether, tetraallyloxyethane, methylenebismethacrylamide, 15-tuply ethoxylated trimethylolpropane triacrylate, polyethylene glycol diacrylate, trimethylolpropane triacrylate and triallylamine.

Very particularly preferred crosslinkers b) are methylenebisacrylamide and the polyethoxylated and/or -propoxylated glycerols which have been esterified with acrylic acid or methacrylic acid to give di- or triacrylates, as described, for example, in WO 2003/104301 A1.

Methylenebisacrylamide and di- and/or triacrylates of 3- to 10-tuply ethoxylated glycerol are particularly advantageous. Very particular preference is given to methylenebisacrylamide, di- or triacrylates of 1- to 5-tuply ethoxylated and/or propoxylated glycerol. Most preferred are methylenebisacrylamide and the triacrylates of 3- to 5-tuply ethoxylated and/or propoxylated glycerol, especially methylenebisacrylamide and the triacrylate of 3-tuply ethoxylated glycerol.

The amount of crosslinker b) is preferably 0.0001% to 0.5% by weight, more preferably 0.001% to 0.2% by weight, most preferably 0.01% to 0.05% by weight, based in each case on monomer a). With rising crosslinker content, the centrifuge retention capacity (CRC) falls and the absorption under a pressure of 21.0 $g/cm^2$ passes through a maximum.

Initiators c) used may be all compounds which generate free radicals under the polymerization conditions, for example thermal initiators, redox initiators or photoinitiators.

Suitable redox initiators are potassium peroxodisulfate or sodium peroxodisulfate/ascorbic acid, hydrogen peroxide/ascorbic acid, potassium peroxodisulfate or sodium peroxodisulfate/sodium bisulfite and hydrogen peroxide/sodium bisulfite. Preference is given to using mixtures of thermal initiators and redox initiators, such as potassium peroxodisulfate or sodium peroxodisulfate/hydrogen peroxide/ascorbic acid. The reducing component used is, however, preferably a mixture of the sodium salt of 2-hydroxy-2-sulfinatoacetic acid, the disodium salt of 2-hydroxy-2-sulfonatoacetic acid and sodium bisulfite. Such mixtures are obtainable as Brüggolite® FF6 and Brüggolite® FF7 (Brüggemann Chemicals; Heilbronn; Germany).

Suitable thermal initiators are especially azo initiators, such as 2,2'-azobis[2-(2-imidazolin-2-yl)propane] dihydrochloride and 2,2'-azobis[2-(5-methyl-2-imidazolin-2-yl)propane] dihydrochloride, 2,2'-azobis(2-amidinopropane) dihydrochloride, 4,4''-azobis(4-cyanopentanoic acid), 4,4' and the sodium salts thereof, 2,2'-azobis[2-methyl-N-(2-hydroxyethyl)propionamide] and 2,2'-azobis(imino-1-pyrrolidino-2-ethylpropane) dihydrochloride.

Suitable photoinitiators are, for example, 2-hydroxy-2-methylpropiophenone and 1-[4-(2-hydroxyethoxy)phenyl]-2-hydroxy-2-methyl-1-propan-1-one.

Ethylenically unsaturated monomers d) copolymerizable with the ethylenically unsaturated monomers a) bearing acid groups are, for example, acrylamide, methacrylamide, hydroxyethyl acrylate, hydroxyethyl methacrylate, dimethylaminoethyl methacrylate, dimethylaminoethyl acrylate, dimethylaminopropyl acrylate, diethylaminopropyl acrylate, dimethylaminoethyl methacrylate, diethylaminoethyl methacrylate.

The water-soluble polymers e) used may be polyvinyl alcohol, polyvinylpyrrolidone, starch, starch derivatives, modified cellulose, such as methyl cellulose or hydroxyethyl cellulose, gelatin, polyglycols or polyacrylic acids, preferably starch, starch derivatives and modified cellulose.

Optionally, one or more chelating agents may be added to the monomer solution or starting materials thereof to mask metal ions, for example iron, for the purpose of stabilization. Suitable chelating agents are, for example, alkali metal citrates, citric acid, alkali metal tartrates, pentasodium triphosphate, ethylenediamine tetraacetate, nitrilotriacetic acid, and also all chelating agents known by the Trilon® name, for example Trilon® C (pentasodium diethylenetriaminepentaacetate), Trilon® D (trisodium (hydroxyethyl) ethylenediaminetriacetate), and Trilon® M (methylglycinediacetic acid).

For optimal action, the preferred polymerization inhibitors require dissolved oxygen. The monomer solution can therefore be freed of dissolved oxygen before the polymerization by inertization, i.e. flowing an inert gas through, preferably nitrogen or carbon dioxide.

If the polymerization is conducted under adequate reflux, the inertization can be dispensed with. In this case, the dissolved oxygen is removed from the polymerization reactor together with the evaporating solvent.

For polymerization, the monomer solution is suspended or emulsified in a hydrophobic solvent.

Usable hydrophobic solvents are all the solvents known to the person skilled in the art for use in suspension polymerization. Preference is given to using aliphatic hydrocarbons, such as n-hexane, n-heptane, n-octane, n-nonane, n-decane, cyclohexane or mixtures thereof. Hydrophobic solvents have a solubility in water at 23° C. of less than 5 g/100 g, preferably less than 1 g/100 g, more preferably less than 0.5 g/100 g.

The hydrophobic solvent boils within the range from preferably 50 to 150° C., more preferably 60 to 120° C., most preferably 70 to 90° C.

The ratio between hydrophobic solvent and monomer solution is 0.2 to 3.0, preferably 0.3 to 2.7 and very preferably from 0.4 to 2.4.

For dispersion of the aqueous monomer solution in the hydrophobic solvent or for dispersion of the water-absorbing polymer particles which form, it is possible to add dispersing aids. These dispersing aids may be anionic, cationic, nonionic or amphoteric surfactants, or natural, semisynthetic or synthetic polymers.

Anionic surfactants are, for example, sodium polyoxyethylene dodecyl ether sulfate and sodium dodecyl ether sulfate. A cationic surfactant is, for example, trimethylstearylammonium chloride. An amphoteric surfactant is, for example, carboxymethyldimethylcetylammonium. Nonionic surfactants are, for example, sucrose fatty acid esters, such as sucrose monostearate and sucrose dilaurate, sorbitan esters such as sorbitan monostearate, trehalose fatty acid esters, such as trehalose stearate, polyoxyalkylene compounds based on sorbitan esters, such as polyoxyethylenesorbitan monostearate.

Suitable polymers are, for example, cellulose derivatives such as hydroxyethyl cellulose, methyl hydroxyethyl cellulose, methyl hydroxypropyl cellulose, methyl cellulose and carboxymethyl cellulose, polyvinylpyrrolidone, copolymers of vinylpyrrolidone, gelatin, gum arabic, xanthan, casein, polyglycerols, polyglycerol fatty acid esters, polyethylene glycols, modified polyethylene glycol such as polyethylene glycol stearate or polyethylene glycol stearyl ether stearate, polyvinyl alcohol, partially hydrolyzed polyvinyl acetates and modified polyethylene, such as a maleic acid-modified polyethylene.

It is also possible to use inorganic particles as dispersing aids, these being called Pickering systems. Such a Pickering system may consist of the solid particles on their own or additionally of auxiliaries which improve the dispersibility of the particles in water or the wettability of the particles by the hydrophobic solvent. The way in which they work and their use are described in WO 99/24525 A1 and EP 1 321 182 A1.

The inorganic solid particles may be metal salts, such as salts, oxides and hydroxides of calcium, magnesium, iron, zinc, nickel, titanium, aluminum, silicon, barium and manganese. These include magnesium hydroxide, magnesium carbonate, magnesium oxide, calcium oxalate, calcium carbonate, barium carbonate, barium sulfate, titanium dioxide, aluminum oxide, aluminum hydroxide and zinc sulfide. These likewise include silicates, bentonite, hydroxyapatite and hydrotalcites. Particular preference is given to $SiO_2$-based silicas, magnesium pyrophosphate and tricalcium phosphate.

Suitable $SiO_2$-based dispersing aids are finely divided silicas. These can be dispersed in water as fine solid particles. It is also possible to use what are called colloidal dispersions of silica in water. Such colloidal dispersions are alkaline aqueous mixtures of silica. In the alkaline pH range, the particles are swollen and stable in water. Preferred colloidal dispersions of silica, at pH 9.3, have a specific surface area in the range from 20 to 90 $m^2/g$.

In addition, it is possible to use any desired mixtures of the dispersing aids.

The dispersing aid is typically dissolved or dispersed in the hydrophobic solvent. The dispersing aid is used in amounts between 0.01 and 10% by weight, preferably between 0.2 and 5% by weight, more preferably between 0.5 and 2% by weight, based on the monomer solution. The diameter of the monomer solution droplets can be adjusted via the type and amount of dispersing aid.

The diameter of the monomer solution droplets can be adjusted via the stirrer energy introduced and through suitable dispersing aids.

The performance of the agglomeration is known to those skilled in the art and is not subject to any restrictions. The polymerization and the agglomeration can be conducted simultaneously (one-stage metering) or successively (two-stage metering).

In the case of one-stage metering, the monomer solution is metered into the hydrophobic solvent and the droplets of monomer solution agglomerate during the polymerization.

In the case of two-stage metering, a first monomer solution is first metered into the hydrophobic solvent and the droplets of monomer solution are polymerized. Then a second monomer solution is metered into the dispersed polymer particles thus obtained and polymerization is effected again. The polymer particles do not agglomerate until the second polymerization. The first and second monomer solutions may be identical or different in terms of composition.

With every further addition of monomer to agglomerates that have already formed, irrespective of whether they have been prepared by one-stage or two-stage metering, the agglomerates can be agglomerated further to give larger agglomerates.

There may be cooling steps between the metered additions of monomer. Some of the dispersing aid may precipitate out therein.

Whether the droplets of the monomer solution agglomerate or not during the polymerization can be established via the type and amount of the dispersing aid. Given a sufficient amount of dispersing aid, agglomeration during the polymerization of the droplets of monomer solution is prevented. The amount necessary for this purpose depends on the type of dispersing aid.

Preference is given to two-stage metered addition, i.e. agglomeration after the polymerization of the droplets of monomer solution.

Advantageously, several stirred reactors are connected in series for the polymerization. Through postreaction in further stirred reactors, the monomer conversion can be increased and backmixing can be reduced. In this context, it is additionally advantageous when the first stirred reactor is not too large. With increasing size of the stirred reactor, there is inevitably broadening of the size distribution of the dispersed monomer solution droplets. A relatively small first reactor therefore enables the production of water-absorbing polymer particles with a particularly narrow particle size distribution.

The reaction is preferably conducted under reduced pressure, for example at a pressure of 800 mbar. The pressure can be used to set the boiling point of the reaction mixture to the desired reaction temperature.

The polymerization can be performed in the presence of a typically water-soluble chain transfer reagent.

Chain transfer reagents intervene in the polymerization kinetics and control the molar mass. Suitable chain transfer reagents are thiols, thiol acids, secondary alcohols, phosphorus compounds, lactic acid, aminocarboxylic acids, etc.

The chain transfer reagent is used in an amount of preferably 0.00001 to 0.1 mol/mol, more preferably of 0.00015 to 0.08 mol/mol, most preferably 0.0002 to 0.06 mol/mol, based in each case on the monomer a).

Addition of the monomer solution may also be above the boiling point of water or of the solvent or the solvent/water azeotrope, such that solvent or a solvent/water azeotrope is distilled off continuously during the addition of monomer.

In a preferred embodiment of the present invention, the water-absorbing polymer particles are dewatered azeotropically in the polymer dispersion and filtered out of the polymer dispersion, and the filtered water-absorbing polymer particles are dried to remove the adhering residual hydrophobic solvent and thermally surface postcrosslinked.

To further improve the properties, the resultant water-absorbing polymer particles may be thermally surface postcrosslinked. The thermal surface postcrosslinking can be conducted in the polymer dispersion or with the water-absorbing polymer particles which have been removed from the polymer dispersion and dried.

Suitable surface postcrosslinkers are compounds which comprise groups which can form covalent bonds with at least two carboxylate groups of the polymer particles. Suitable compounds are, for example, polyfunctional amines, polyfunctional amido amines, polyfunctional epoxides, as described in EP 0 083 022 A2, EP 0 543 303 A1 and EP 0 937 736 A2, di- or polyfunctional alcohols, as described in DE 33 14 019 A1, DE 35 23 617 A1 and EP 0 450 922 A2, or β-hydroxyalkylamides, as described in DE 102 04 938 A1 and U.S. Pat. No. 6,239,230.

Additionally described as suitable surface postcrosslinkers are alkylene carbonates in DE 40 20 780 C1, 2-oxazolidinone and derivatives thereof, such as 2-hydroxyethyl-2-oxazolidinone, in DE 198 07 502 A1, bis- and poly-2-oxazolidinones in DE 198 07 992 C1, 2-oxotetrahydro-1,3-oxazine and derivatives thereof in DE 198 54 573 A1, N-acyl-2-oxazolidinones in DE 198 54 574 A1, cyclic ureas in DE 102 04 937 A1, bicyclic amido acetals in DE 103 34 584 A1, oxetanes and cyclic ureas in EP 1 199 327 A2 and morpholine-2,3-dione and derivatives thereof in WO 2003/031482 A1.

In addition, it is also possible to use surface postcrosslinkers which comprise additional polymerizable ethylenically unsaturated groups, as described in DE 37 13 601 A1.

In addition, it is possible to use any desired mixtures of the suitable surface postcrosslinkers.

Preferred surface postcrosslinkers are alkylene carbonates, 2-oxazolidinones, bis- and poly-2-oxazolidinones, 2-oxotetrahydro-1,3-oxazines, N-acyl-2-oxazolidinones, cyclic ureas, bicyclic amido acetals, oxetanes, bisoxetanes and morpholine-2,3-diones.

Particularly preferred surface postcrosslinkers are ethylene carbonate (1,3-dioxolan-2-one), trimethylene carbonate (1,3-dioxan-2-one), 3-methyl-3-oxethanemethanol, 2-hydroxyethyl-2-oxazolidinone, 2-oxazolidinone and methyl-2-oxazolidinone.

Very particular preference is given to ethylene carbonate.

The amount of surface postcrosslinker is preferably 0.1% to 10% by weight, more preferably 0.5% to 7.5% by weight and most preferably 1% to 5% by weight, based in each case on the polymer particles.

The surface postcrosslinkers are typically used in the form of an aqueous solution. The amount of the solvent is preferably 0.001 to 8% by weight, more preferably 2 to 7% by weight, even more preferably 3 to 6% by weight and especially 4 to 5% by weight, based in each case on the polymer particles. The penetration depth of the surface postcrosslinker into the polymer particles can be adjusted via the content of nonaqueous solvent and total amount of solvent.

When exclusively water is used as the solvent, a surfactant is advantageously added. This improves the wetting characteristics and reduces the tendency to form lumps. However, preference is given to using solvent mixtures, for example isopropanol/water, 1,3-propanediol/water and propylene glycol/water, where the mixing ratio in terms of mass is preferably from 10:90 to 60:40.

In a preferred embodiment of the present invention, cations, especially polyvalent cations, are applied to the particle surface in addition to the surface postcrosslinkers before, during or after the thermal surface postcrosslinking.

The polyvalent cations usable in the process according to the invention are, for example, divalent cations such as the cations of zinc, magnesium, calcium, iron and strontium, trivalent cations such as the cations of aluminum, iron, chromium, rare earths and manganese, tetravalent cations such as the cations of titanium and zirconium. Possible counterions are hydroxide, chloride, bromide, sulfate, hydrogensulfate, carbonate, hydrogencarbonate, nitrate, phosphate, hydrogenphosphate, dihydrogenphosphate and carboxylate, such as acetate, citrate and lactate. Salts with different counterions are also possible, for example basic aluminum salts such as aluminum monoacetate or aluminum monolactate. Aluminum sulfate, aluminum monoacetate and aluminum lactate are preferred. Apart from metal salts, it is also possible to use polyamines as polyvalent cations.

The amount of polyvalent cation used is, for example, 0.001% to 1.5% by weight, preferably 0.005% to 1% by weight and more preferably 0.02% to 0.8% by weight, based in each case on the polymer particles.

The surface postcrosslinking is typically performed in such a way that a solution of the surface postcrosslinker is sprayed onto the dried polymer particles. After the spray application, the surface postcrosslinker-coated polymer particles are thermally surface postcrosslinked.

The spray application of a solution of the surface postcrosslinker is preferably performed in mixers with moving mixing tools, such as screw mixers, disk mixers and paddle mixers. Particular preference is given to horizontal mixers such as paddle mixers, very particular preference to vertical mixers. The distinction between horizontal mixers and vertical mixers is made by the position of the mixing shaft, i.e. horizontal mixers have a horizontally mounted mixing shaft and vertical mixers a vertically mounted mixing shaft. Suitable mixers are, for example, horizontal Pflugschar® plowshare mixers (Gebr. Lodige Maschinenbau GmbH; Paderborn; Germany), Vrieco-Nauta continuous mixers (Hosokawa Micron BV; Doetinchem; the Netherlands), Processall Mixmill mixers (Processall Incorporated; Cincinnati; USA) and Schugi Flexomix® (Hosokawa Micron BV; Doetinchem; the Netherlands). However, it is also possible to spray on the surface postcrosslinker solution in a fluidized bed.

The thermal surface postcrosslinking is preferably performed in contact driers, more preferably paddle driers, most preferably disk driers. Suitable driers are, for example, Hosokawa Bepex® Horizontal Paddle Dryers (Hosokawa Micron GmbH; Leingarten; Germany), Hosokawa Bepex® Disc Dryers (Hosokawa Micron GmbH; Leingarten; Germany), Holo-Flite® driers (Metso Minerals Industries Inc.; Danville; USA) and Nara Paddle Dryers (NARA Machinery Europe; Frechen; Germany). Moreover, fluidized bed driers may also be used.

The thermal surface postcrosslinking can be effected in the mixer itself, by heating the jacket or blowing in warm air. Equally suitable is a downstream drier, for example a shelf drier, a rotary tube oven or a heatable screw. It is particularly advantageous to effect mixing and thermal surface postcrosslinking in a fluidized bed drier.

It may be advantageous to conduct the thermal surface postcrosslinking under reduced pressure or to conduct it with use of drying gases, for example dried air and nitrogen, in order to ensure the very substantial removal of the solvents.

Subsequently, the surface postcrosslinked polymer particles can be classified, with removal of excessively small and/or excessively large polymer particles and recycling thereof into the process.

The surface postcrosslinking can also be conducted in the polymer dispersion. For this purpose, the solution of the surface postcrosslinker is added to the polymer dispersion. In this context, it may be advantageous to conduct the thermal surface postcrosslinking under elevated pressure, for example with use of hydrophobic organic solvents having a boiling point at 1013 mbar below the desired temperature for the thermal surface postcrosslinking. After the thermal surface postcrosslinking in the polymer dispersion, the water-absorbing polymer particles are dewatered azeotropically in the polymer dispersion and removed from the polymer dispersion, and the water-absorbing polymer particles removed are dried to remove the adhering residual hydrophobic solvent.

Preferred surface postcrosslinking temperatures are in the range of 100 to 220° C., preferably in the range of 105 to 210° C., more preferably in the range of 110 to 205° C., most preferably in the range of 120 to 200° C. The preferred residence time at this temperature is preferably at least 10 minutes, more preferably at least 20 minutes, most preferably at least 30 minutes, and typically at most 120 minutes.

In a further preferred embodiment of the present invention, hydrophilizing agents are additionally applied before, during or after the thermal surface postcrosslinking, for example sugar alcohols such as sorbitol, mannitol and xylitol, water-soluble polymers or copolymers such as cellulose, polyethylene glycols, polyvinyl alcohols, polyvinylpyrrolidones and polyacrylamides.

In a preferred embodiment of the present invention, the water-absorbing polymer particles are cooled after the thermal surface postcrosslinking in a contact drier. The cooling is preferably performed in contact coolers, more preferably paddle coolers and most preferably disk coolers. Suitable coolers are, for example, Hosokawa Bepex® Horizontal Paddle Cooler (Hosokawa Micron GmbH; Leingarten; Germany), Hosokawa Bepex® Disc Cooler (Hosokawa Micron GmbH; Leingarten; Germany), Holo-Flite® coolers (Metso Minerals Industries Inc.; Danville; USA) and Nara Paddle Cooler (NARA Machinery Europe; Frechen; Germany). Moreover, fluidized bed coolers may also be used.

In the cooler, the water-absorbing polymer particles are cooled to 20 to 150° C., preferably 30 to 120° C., more preferably 40 to 100° C. and most preferably 50 to 80° C.

To further improve the properties, the polymer particles thermally surface postcrosslinked in a contact drier can be coated or remoisturized.

The remoisturizing is preferably performed at 30 to 80° C., more preferably at 35 to 70° C., most preferably at 40 to 60° C. At excessively low temperatures, the water-absorbing polymer particles tend to form lumps, and, at higher temperatures, water already evaporates to a noticeable degree. The amount of water used for remoisturizing is preferably from 1 to 10% by weight, more preferably from 2 to 8% by weight and most preferably from 3 to 5% by weight. The remoisturizing increases the mechanical stability of the polymer particles and reduces their tendency to static charging.

Suitable coatings for improving the free swell rate and the permeability (SFC) are, for example, inorganic inert substances, such as water-insoluble metal salts, organic polymers, cationic polymers and di- or polyvalent metal cations. Suitable coatings for dust binding are, for example, polyols. Suitable coatings for counteracting the undesired caking tendency of the polymer particles are, for example, fumed silica, such as Aerosil® 200, and surfactants, such as Span® 20 and Plantacare 818 UP and surfactant mixtures.

The present invention further provides the water-absorbing polymer particles obtainable by the process according to the invention.

The water-absorbing polymer particles obtainable by the process according to the invention have a centrifuge retention capacity (CRC) of 50 to 80 g/g, a vortex of 30 to 60 s, a median particle size of 200 to 350 µm, a breadth of the particle size distribution ($\sigma_\xi$) of less than 0.8 and a bulk density of 0.8 to 1.0 g/cm$^3$.

The inventive water-absorbing polymer particles have a centrifuge retention capacity (CRC) of preferably 52 to 75 g/g, more preferably 54 to 70 g/g and most preferably 55 to 65 g/g.

The inventive water-absorbing polymer particles have a vortex of preferably 34 to 58 s, more preferably 38 to 54 g/g and most preferably 40 to 50 g/g.

The inventive water-absorbing polymer particles have a median particle size of preferably 220 to 330 µm, more preferably 240 to 310 µm and most preferably 250 to 300 µm.

The inventive water-absorbing polymer particles have a breadth of the particle size distribution ($\sigma_\xi$) of preferably less than 0.7, more preferably less than 0.6 and most preferably less than 0.5.

The inventive water-absorbing polymer particles have a bulk density of preferably 0.82 to 0.98 g/cm$^3$, more preferably 0.84 to 0.96 g/cm$^3$ and most preferably 0.85 to 0.95 g/cm$^3$.

The water-absorbing polymer particles obtainable by the process according to the invention preferably have a centrifuge retention capacity (CRC) of 52 to 75 g/g, a vortex of 34 to 58 s, a median particle size of 220 to 330 µm, a breadth of the particle size distribution ($\sigma_\xi$) of less than 0.7 and a bulk density of 0.82 to 0.98 g/cm³.

The water-absorbing polymer particles obtainable by the process according to the invention more preferably have a centrifuge retention capacity (CRC) of 54 to 70 g/g, a vortex of 38 to 54 s, a median particle size of 240 to 310 μm, a breadth of the particle size distribution ($\sigma_\xi$) of less than 0.6 and a bulk density of 0.84 to 0.96 g/cm³.

The water-absorbing polymer particles obtainable by the process according to the invention most preferably have a centrifuge retention capacity (CRC) of 55 to 65 g/g, a vortex of 40 to 50 s, a median particle size of 250 to 300 μm, a breadth of the particle size distribution ($\sigma_\xi$) of less than 0.5 and a bulk density of 0.85 to 0.95 g/cm³.

The present invention further provides hygiene articles comprising (A) an upper liquid-impermeable layer,
(B) a lower liquid-permeable layer,
(C) a liquid-absorbing storage layer between layer (A) and layer (B), comprising from 0 to 30% by weight of a fibrous material and from 70 to 100% by weight of water-absorbing polymer particles obtainable by the process according to the invention,
(D) optionally an acquisition and distribution layer between layer (A) and layer (C), comprising from 80 to 100% by weight of a fibrous material and from 0 to 20% by weight of water-absorbing polymer particles obtainable by the process according to the invention,
(E) optionally a fabric layer directly above and/or beneath layer (C) and
(F) further optional components.

The proportion of water-absorbing polymer particles obtainable by the process according to the invention in the liquid-absorbing storage layer (C) is preferably at least 75% by weight, more preferably at least 80% by weight, most preferably at least 90% by weight.

The mean sphericity of the water-absorbing polymer particles obtainable by the process according to the invention in the liquid-absorbing storage layer (C) is preferably less than 0.84, more preferably less than 0.82, most preferably less than 0.80.

Water-absorbing polymer particles having relatively low sphericity are obtained by suspension polymerization when the polymer particles are agglomerated during or after the polymerization.

In the inventive hygiene articles, agglomerated water-absorbing polymer particles are used.

The water-absorbing polymer particles are tested by means of the test methods described below.

Methods:

The measurements should, unless stated otherwise, be conducted at an ambient temperature of 23±2° C. and a relative air humidity of 50±10%. The water-absorbing polymers are mixed thoroughly before the measurement.

Moisture Content

The moisture content of the water-absorbing polymer particles is determined by EDANA recommended test method No. WSP 230.3 (11) "Mass Loss Upon Heating".

Centrifuge Retention Capacity

The centrifuge retention capacity (CRC) is determined by EDANA recommended test method No. WSP 241.3(11) "Fluid Retention Capacity in Saline, After Centrifugation".

Bulk Density

The bulk density is determined by EDANA recommended test method No. WSP 250.3 (11) "Gravimetric Determination of Density".

Vortex Test 50.0 ml±1.0 ml of a 0.9% by weight aqueous sodium chloride solution are introduced into a 100 ml beaker which comprises a magnetic stirrer bar of size 30 mm×6 mm. A magnetic stirrer is used to stir the sodium chloride solution at 600 rpm. Then 2.000 g±0.010 g of water-absorbing polymer particles are added as rapidly as possible, and the time taken for the stirrer vortex to disappear as a result of the absorption of the sodium chloride solution by the water-absorbing polymer particles is measured. When measuring this time, the entire contents of the beaker may still be rotating as a homogeneous gel mass, but the surface of the gelated sodium chloride solution must no longer exhibit any individual turbulences. The time taken is reported as the vortex.

Measurement of Dissolved Oxygen

The concentration of dissolved oxygen was measured with an oxygen meter of the SevenGo Pro® SG6 type (Mettler Toledo GmbH; Giessen; Germany). The total oxygen concentrations are calculated as follows:

$$c_{tot1} = (m_{M1} \times c_{M1} + m_{org} \times c_{org1})/(m_{M1} + m_{org})$$

or $$c_{tot2} = (m_{M2} \times c_{M2} + (m_{M1} + m_{org}) \times c_{org2})/(m_{M2} + m_{M1} + m_{org})$$

where:
$m_{M1}$=mass of monomer solution for metered addition 1 (polymerization) in g
$m_{M2}$=mass of monomer solution for metered addition 2 (agglomeration) in g
$m_{org}$=mass of organic solution in g
$c_{M1}$=oxygen concentration of monomer solution for metered addition 1 (polymerization) in ppm
$c_{M2}$=oxygen concentration of monomer solution for metered addition 2 (agglomeration) in ppm
$c_{org1}$=oxygen concentration of organic solution prior to metered addition 1 in ppm
$c_{org1}$=oxygen concentration of organic solution prior to metered addition 2 in ppm
$c_{tot1}$=total oxygen concentration after metered addition 1 has ended
$c_{tot2}$=total oxygen concentration after metered addition 2 has ended The oxygen concentration of the monomer solution cannot be measured again after the polymerization has started and therefore has to be measured beforehand.

Particle Size Distribution

The median particle size and the breadth of the particle size distribution ($\sigma_\xi$) were determined analogously to EP 0 349 240 B1, using sieves having mesh sizes of 100 μm, 200 μm, 300 μm, 400 μm, 450 μm, 500 μm, 600 μm, 710 μm, 800 μm, 900 μm, 1000 μm, 1180 μm, 1400 μm, 1600 μm, 1700 μm, 2000 μm and 4000 μm.

The narrower the particle size distribution, the smaller the values for the particle size distribution a.

Mean Sphericity (mSPHT)

The mean sphericity (mSPHT) is determined with the PartAn® 3001 L particle analyzer (Microtrac Europe GmbH; DE).

The sample to be analyzed is introduced into a funnel. The computer-controlled measurement system starts the metering device and ensures a continuous, concentration-regulated particle flow. The particles fall individually through the measurement shaft and generate high-contrast shadow images between light source and high-resolution camera. The light source is actuated by the camera and, because of very short exposure times, produces faultless image information for the multiple evaluation of each individual particle in real time.

In a 3D process, each particle is analyzed repeatedly and the process thus gives the absolute results for length, width, thickness, area and circumference. The number of pixels covered by the particle is used to calculate the size and shape. This also results in the comparatively precise determination of the mean sphericity (mSPHT).

Production of the Base Polymer:

EXAMPLE 1

A 2 L flange vessel equipped with impeller stirrer and reflux condenser was initially charged with 340.00 g of heptane and 0.92 g of sucrose stearate (Ryoto® Sugar Ester S-370, Mitsubishi Chemical Europe GmbH, Dusseldorf, Germany), and heated to 70° C. until the sucrose stearate had dissolved fully. The oxygen concentration of the organic solution $c_{org1}$ was 8.5 ppm.

A monomer solution (first metered addition), prepared from 73.40 g (1.019 mol) of acrylic acid, 61.20 g (0.765 mol) of 50% by weight aqueous sodium hydroxide solution, 109.5 g of water and 0.11 g (0.407 mmol) of potassium peroxodisulfate, was then introduced into a feed vessel. The oxygen concentration of the monomer solution $c_{M1}$ was 8.5 ppm. Immediately prior to the dropwise addition of the monomer solution (over a period of 15 min), a stirrer speed of 300 rpm and an oil bath temperature of 55° C. were established.

After feeding had ended, the mixture was stirred while introducing nitrogen at 16 L/h at 70° C. for a further hour, then the reaction solution was cooled to about 25° C. and an ice-cooled monomer solution (second metered addition), prepared from 95.90 g (1.331 mol) of acrylic acid, 79.30 g (0.991 mol) of 50% by weight aqueous sodium hydroxide solution, 143.10 g of water and 0.14 g (0.518 mmol) of potassium peroxodisulfate, was introduced into a feed vessel. The oxygen concentration of the organic solution $c_{org1}$ was 0.1 ppm. The oxygen concentration of the monomer solution $c_{M2}$ was 9.1 ppm. The monomer solution was added dropwise within 15 minutes.

After the feeding had ended, an oil bath temperature of 70° C. was established while introducing nitrogen at 16 L/h. 120 minutes after commencement of heating, the reflux condenser was exchanged for a water separator and water was separated out.

The suspension present was cooled to 60° C. and the resultant polymer particles were filtered off with suction using a Büchner funnel with a paper filter. The further drying was effected at 45° C. in an air circulation drying cabinet and optionally in a vacuum drying cabinet at 800 mbar down to a residual moisture content of less than 15% by weight.

The properties of the resulting polymer particles are summarized in table 2.

EXAMPLES 2 TO 5

The base polymer was produced analogously to example 1, with selection of the nitrogen purge rate and times such that the oxygen concentrations specified in table 1 were present, respectively, in the monomer solution and in the organic phase immediately prior to the dropwise addition of the first and second metered additions.

The properties of the resulting polymer particles are summarized in table 2.

EXAMPLE 6

A 2 L flange vessel equipped with impeller stirrer and reflux condenser was initially charged with 340.00 g of heptane and 0.92 g of sucrose stearate (Ryoto® Sugar Ester S-370, Mitsubishi Chemical Europe GmbH, Dusseldorf, Germany), and heated to 70° C. until the sucrose stearate had dissolved fully. Subsequently, inertization was effected by nitrogen purging at 16 L/h. The oxygen concentration of the organic solution $c_{org1}$ was 0.1 ppm.

A monomer solution (first metered addition), prepared from 73.40 g (1.019 mol) of acrylic acid, 61.20 g (0.765 mol) of 50% by weight aqueous sodium hydroxide solution, 109.5 g of water, 0.018 g (0.117 mmol) of N,N'-methylenebisacrylamide (MBA) and 0.11 g (0.407 mmol) of potassium peroxodisulfate, was then introduced into a feed vessel. The oxygen concentration of the monomer solution $c_{M1}$ was 8.5 ppm. Immediately prior to the dropwise addition of the monomer solution (over a period of 15 min), a stirrer speed of 300 rpm and an oil bath temperature of 55° C. were established.

After feeding had ended, the mixture was stirred while introducing nitrogen at 16 L/h at 70° C. for a further hour, then the reaction solution was cooled to about 25° C. and an ice-cooled monomer solution (second metered addition), prepared from 95.90 g (1.331 mol) of acrylic acid, 79.30 g (0.991 mol) of 50% by weight aqueous sodium hydroxide solution, 143.10 g of water, 0.023 g (0.149 mmol) of N,N'-methylenebisacrylamide (MBA) and 0.14 g (0.518 mmol) of potassium peroxodisulfate, was introduced into a feed vessel. The oxygen concentration of the organic solution $c_{org1}$ was 0.1 ppm. The oxygen concentration of the monomer solution $c_{M2}$ was 9.0 ppm. The monomer solution was added dropwise within 15 minutes.

After the feeding had ended, an oil bath temperature of 70° C. was established while introducing nitrogen at 16 L/h. 120 minutes after commencement of heating, the reflux condenser was exchanged for a water separator and water was separated out.

The suspension present was cooled to 60° C. and the resultant polymer particles were filtered off with suction using a Büchner funnel with a paper filter. The further drying was effected at 45° C. in an air circulation drying cabinet and optionally in a vacuum drying cabinet at 800 mbar down to a residual moisture content of less than 15% by weight.

The properties of the resulting polymer particles are summarized in table 2.

EXAMPLES 7 TO 12

The base polymer was produced analogously to example 6, with selection of the nitrogen purge rate and times such that the oxygen concentrations specified in table 1 were present, respectively, in the monomer solution and in the organic phase immediately prior to the dropwise addition of the first and second metered additions.

The properties of the resulting polymer particles are summarized in table 2.

TAB. 1

| | Oxygen concentrations | | | | | |
|---|---|---|---|---|---|---|
| Ex. | $c_{M1}$ ppm | $c_{M2}$ ppm | $c_{org1}$ ppm | $c_{org2}$ ppm | $c_{tot1}$ ppm | $c_{tot2}$ ppm |
| 1 | 8.5 | 9.1 | 8.5 | 0.1 | 8.5 | 3.3 |
| 2 | 8.5 | 3.3 | 8.5 | 0.1 | 8.5 | 1.2 |

TAB. 1-continued

Oxygen concentrations

| Ex. | $c_{M1}$ ppm | $c_{M2}$ ppm | $c_{org1}$ ppm | $c_{org2}$ ppm | $c_{tot1}$ ppm | $c_{tot2}$ ppm |
|---|---|---|---|---|---|---|
| 3  | 4.0 | 4.0 | 8.5 | 0.1 | 6.6 | 1.5 |
| 4  | 3.0 | 3.0 | 8.5 | 0.1 | 6.2 | 1.1 |
| 5  | 2.0 | 2.0 | 8.5 | 0.1 | 5.8 | 0.8 |
| 6  | 8.5 | 9.0 | 0.1 | 0.1 | 3.6 | 3.2 |
| 7  | 7.0 | 5.9 | 0.1 | 0.1 | 3.0 | 2.1 |
| 8  | 6.0 | 6.0 | 0.1 | 0.1 | 2.6 | 2.2 |
| 9  | 5.0 | 5.1 | 0.1 | 0.1 | 2.1 | 1.9 |
| 10 | 4.0 | 4.1 | 0.1 | 0.1 | 1.7 | 1.5 |
| 11 | 3.0 | 3   | 0.1 | 0.1 | 1.3 | 1.1 |
| 12 | 2.1 | —   | 0.1 | 0.1 | 0.9 | —   |

TAB. 2

Properties of the water-absorbing polymer particles

| Ex. | CRC g/g | Vortex s | Bulk density g/100 mL | Moisture content g/g | Median particle size μm | Particle size distribution $\sigma_\xi$ | Particles >1000 μm % by wt. |
|---|---|---|---|---|---|---|---|
| 1     | 45.1 | 52  | 84 | 4.9 | 325  | 0.293 | 2   |
| 2     | 53.4 | 53  | 80 | 2.3 | 284  | 0.292 | 4   |
| 3     | 52.8 | 37  | 89 | 2.7 | 281  | 0.263 | 1   |
| 4     | 60.1 | 47  | 90 | 1.9 | 268  | 0.486 | 2   |
| 5     | 60.3 | 46  | 90 | 1.8 | 246  | 0.474 | 1   |
| 6     | 46.1 | 185 | 92 | 2   | 593  | 0.484 | 15  |
| 7     | 46.0 | 95  | 82 | 2.3 | 555  | 0.669 | 17  |
| 8     | nd   | nd  | 98 | 2.5 | 1850 | 1.100 | 65  |
| 9     | nd   | nd  | 94 | 1.8 | 1700 | 0.838 | 71  |
| 10*)  | nd   | nd  | nd | nd  | nd   | nd    | 100 |
| 11*)  | nd   | nd  | nd | nd  | nd   | nd    | 100 |
| 12**) | nd   | nd  | nd | nd  | nd   | nd    | 100 | nd not determined
*)complete agglomeration or coagulation during the agglomeration
**)complete agglomeration or coagulation during the polymerization

The invention claimed is:

1. A process for producing water-absorbing polymer particles by polymerizing a monomer solution comprising
   a) at least one ethylenically unsaturated monomer which bears an acid group and may have been at least partly neutralized,
   b) optionally one or more crosslinker,
   c) at least one initiator,
   d) optionally one or more ethylenically unsaturated monomer copolymerizable with the monomer mentioned under a) and
   e) optionally one or more water-soluble polymer,
   with the monomer solution suspended in a hydrophobic organic solvent during the polymerization, and being agglomerated in the hydrophobic organic solvent during or after the polymerization, wherein the polymerization is conducted in the presence of dissolved oxygen, wherein the resultant water-absorbing polymer particles are at least one partly dewatered azeotropically after the agglomeration and wherein the resultant water-absorbing polymer particles are filtered and dried after the azeotropic dewatering.

2. The process according to claim 1, wherein a total oxygen concentration $c_{tot1}$ after addition of the monomer solution to the polymerization is at least 2 ppm.

3. The process according to claim 1, wherein an oxygen concentration in the hydrophobic organic solvent $C_{org1}$ after addition of the monomer solution to the polymerization is at least 2 ppm.

4. The process according to claim 1, wherein an oxygen concentration in the hydrophobic organic solvent $C_{org1}$ used in the polymerization is from 5 to 10 ppm.

5. The process according to claim 1, wherein an oxygen concentration in the monomer solution $C_{M1}$ used in the polymerization is up to 10 ppm.

6. The process according to claim 1, wherein an oxygen concentration in the monomer solution $C_{M1}$ used in the polymerization is from 3 to 8 ppm.

7. The process according to claim 1, wherein the water-absorbing polymer particles obtained after the polymerization are agglomerated in the hydrophobic organic solvent with addition of a second monomer solution.

8. The process according to claim 7, wherein a total oxygen concentration $c_{tot2}$ after the addition of the second monomer solution used in the agglomeration is less than 4 ppm.

9. The process according to claim 7, wherein a total oxygen concentration $C_{tot2}$ after the addition of the second monomer solution is used in the agglomeration is less than 2 ppm.

10. The process according to claim 7, wherein an oxygen concentration in the hydrophobic organic solvent $C_{org2}$ used in the agglomeration is less than 2 ppm.

11. The process according to claim 7, wherein an oxygen concentration of the second monomer solution $C_{M2}$ used in the agglomeration is less than 12 ppm.

12. The process according to claim 7, wherein a total oxygen concentration of the second monomer solution $C_{M2}$ used in the agglomeration is less than 6 ppm.

* * * * *